(12) United States Patent
Ma et al.

(10) Patent No.: US 10,106,815 B2
(45) Date of Patent: Oct. 23, 2018

(54) **FUSARIUM HEAD BLIGHT RESISTANT GENE *TAFHB1* OF WHEAT AND USE THEREOF**

(71) Applicant: NANJING AGRICULTURAL UNIVERSITY, Nanjing, Jiangsu (CN)

(72) Inventors: Zhengqiang Ma, Nanjing (CN); Guoqiang Li, Nanjing (CN); Haiyan Jia, Nanjing (CN); Shulin Xue, Nanjing (CN); Zhongxin Kong, Nanjing (CN); Na Li, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 0 days.

(21) Appl. No.: 15/413,299

(22) Filed: Jan. 23, 2017

(65) Prior Publication Data

US 2017/0211090 A1    Jul. 27, 2017

(30) Foreign Application Priority Data

Jan. 22, 2016 (CN) .......................... 2016 1 0046023

(51) Int. Cl.
| | |
|---|---|
| *C12N 15/82* | (2006.01) |
| *A01H 5/00* | (2018.01) |
| *A01H 5/10* | (2018.01) |
| *C07K 14/415* | (2006.01) |

(52) U.S. Cl.
CPC ........... *C12N 15/8282* (2013.01); *A01H 5/00* (2013.01); *A01H 5/10* (2013.01); *C07K 14/415* (2013.01)

(58) Field of Classification Search
CPC ..... C12N 15/8282; C07K 14/415; A01H 5/10
See application file for complete search history.

(56) References Cited

U.S. PATENT DOCUMENTS

| | | | | |
|---|---|---|---|---|
| 2003/0236208 A1* | 12/2003 | Kmiec | ................. | C12N 15/102 514/44 R |
| 2006/0070143 A1* | 3/2006 | Marshall | .................. | A01H 5/10 800/287 |

FOREIGN PATENT DOCUMENTS

| | | | | |
|---|---|---|---|---|
| WO | WO2015184331 | * | 12/2015 | ............. C12N 15/82 |
| WO | WO-2015184331 A2 | * | 12/2015 | ............... A01H 5/00 |

OTHER PUBLICATIONS

Rawat, Nidhi, et al. "Wheat Fhb1 encodes a chimeric lectin with agglutinin domains and a pore-forming toxin-like domain conferring resistance to Fusarium head blight." Nature genetics 48.12 (2016): 1576-1580 (Year: 2016).*
Brenchley, Rachel, et al. "Analysis of the bread wheat genome using whole-genome shotgun sequencing." Nature 491.7426 (2012):705. (Year: 2012).*
Zhivko Atanassov et al; "Mycotoxin production and pathogenicity of *Fusarium* species and wheat resistance to Fusarium head blight" Can. J. Bot.; 1994; vol. 72; pp. 161-167.
J.W. Bennett et al; "Mycotoxins;" Clinical Microbiology Reviews; Jul. 2003; vol. 16; No. 3; pp. 497-516.
H. Buerstmayr et al; "QTL mapping and marker-assisted selection for Fusarium head blight resistance in wheat: a review;" Plant Breeding; 2009; vol. 128; pp. 1-26.
Etienne Duveiller et al; "Global Fusarium Networking;" 3rd Int. FHB Symposium; 2008; pp. 11-19.
F. Lin et al; "Mapping QTL associated with resistance to Fusarium head blight in the Nanda2419 x Wangshuibai population. I. Type II resistance;" Theor Appl Genet; 2004; vol. 109; pp. 1504-1511.
Sixin Liu et al; "Complex microcolinearity among wheat, rice, and barley revealed by fine mapping of the genomic region harboring a major QTL for resistance to Fusarium head blight in wheat" Funct Integr Genomics; 2006; vol. 6; pp. 83-89.
Marcia McMullen et al; "Scab of Wheat and Barley: A Re-emerging Disease of Devastating Impact" Plant Disease; vol. 81; No. 12; pp. 1340-1348.
T. Miedaner et al; "Effects of genotype and genotype-environment interaction on deoxynivalenol accumulation and resistance to Fusarium head blight in rye, triticale, and wheat;" Plant Breeding; 2001; vol. 120; pp. 97-105.
Stoyan R. Pirgozliev et al; "Strategies for the control of Fusarium head blight in cereals;" European Journal of Plant Pathology; 2003; vol. 109; pp. 731-742.
Alain Verstraete; "Fourth Symposium on Workplace Drug Testing;" Forensic Science International; 2008; vol. 174; pp. 89.
Carol E. Windels; "Economic and Social Impacts of Fusarium Head Blight: Changing Farms and Rural Communities in the Northern Great Plains;" The American Phytopathological Society; 2000; vol. 90; No. 1; pp. 17-21.

* cited by examiner

*Primary Examiner* — Lee A Visone
*Assistant Examiner* — Weihua Fan
(74) *Attorney, Agent, or Firm* — Oliff PLC

(57) ABSTRACT

A *Fusarium* head blight (FHB) resistant gene Tafhb1 of wheat and uses thereof are disclosed, in which the FHB resistant gene Tafhb1 of wheat has a cDNA sequence as shown in SEQ ID NO. 1. A protein TaFHB1 encoded by the FHB resistant gene Tafhb1 of wheat has an amino acid sequence as shown in SEQ ID NO. 2. The protein includes 274 amino acids, and has an isoelectric point of 10.85. The FHB resistant gene Tafhb1 of wheat is transferred to wheat by crossing and multiple generations of backcrossing, to increase the resistance of wheat to FHB. Because the gene is an endogenous gene existing in the cereal crop wheat, the presence of the gene has no influence on the food safety of plants, such that the gene can be used in crop breeding.

3 Claims, 2 Drawing Sheets
Specification includes a Sequence Listing.

FUSARIUM HEAD BLIGHT RESISTANT GENE *TAFHB1* OF WHEAT AND USE THEREOF

BACKGROUND

Technical Field

The present invention relates to the field of molecular breeding, and particular to a *Fusarium* head blight resistant gene Tafhb1 of wheat and use thereof.

Related Art

*Fusarium* head blight (FHB) caused by *Fusarium graminearum* Schwabe is a disease common to wheat, corn, rice, barley and other main food crops, and takes place worldwide. The disease can destroy a high yield wheat variety in several weeks during the mature stage of wheat, causing yield loss and declined quality (Windels, 2000). Because the wheat grain infected with the pathogen contains a large amount of trichothecene and fungal toxins harmful to animals and human, acute adverse effects occur to animals after intake, such as food refusal, diarrhea, vomiting, gastrointestinal bleeding and contact dermatitis (Bennett and Klich 2003). Therefore, they are no longer suitable for consumption (Atanassozv et al. 1994; McMullen et al. 1997; Miedaneret et al. 2010). The contents of trichothecene and fungal toxins in cereals is restricted in numerous countries and regions including China, the European Union and the United States (Verstraete 2008). With the change of climate and the promotion of crop rotation system, the incidence of FHB on wheat spreads rapidly. The research on FHB of wheat receives great attention in the past few years (Duveiller et al. 2008). In contrast to the use of fungicide, breeding FHB resistant wheat cultivars is the most effective and environmentally friendly strategy for controlling the FHB in wheat (McMullen et al. 1997; Pirgozliev et al. 2003).

Many researches showed that FHB resistance of wheat is a quantitative trait (Buerstmayr et al. 2009). At present, seven FHB resistant QTLs/genes are successfully mapped and denominated. However, no FHB resistant QTL has been cloned. A FHB resistant major QTL was identified in FHB resistant germplasm Wangshuibai from Jiangsu, China, which is mapped between Xbarc147.1 and Xgwm493 (Lin et al. 2004), and designated as Fhb1 (Liu et al. 2006).

SUMMARY

In view of the defects existing in the prior art, an object of the present invention is to provide a FHB resistant gene Tafhb1 of wheat.

Another object of the present invention is to provide a protein TaFHB1 encoded by the FHB resistant gene Tafhb1 of wheat.

Another object of the present invention is to provide use of the FHB resistant gene Tafhb1 of wheat.

The objects of the present invention are accomplished by means of the following technical methods.

A FHB resistant gene Tafhb1 of wheat is provided, the cDNA of which is as shown in SEQ ID NO. 1.

A protein TaFHB1 encoded by the FHB resistant gene Tafhb1 of wheat according to the present invention is provided, which has an amino acid sequence as shown in SEQ ID NO. 2, corresponding 274 amino acids, and has an isoelectric point of 10.85.

For the gene encoding the protein TaFHB1 according to the present invention, the nucleotide sequence comprises, but is not limited to, that shown in SEQ ID NO. 1, and may also be other codon optimised nucleotide sequences encoding the protein TaFHB1.

Use of the FHB resistant gene Tafhb1 of wheat according to the present invention in the improvement of the FHB resistance in wheat is provided.

Use of the FHB resistant gene Tafhb1 according to the present invention in the improvement of the FHB resistance in Triticeae is provided.

The FHB resistant gene Tafhb1 according to the present invention is preferably used in the improvement of the FHB resistance in rice, corn, barley, rye, soybean, and other plants.

BENEFICIAL EFFECTS

The present invention provides a new FHB resistant gene Tafhb1 of wheat and a protein TaFHB1 encoded by the same. The FHB resistant gene Tafhb1 of wheat according to the present invention is transferred to wheat by crossing and multiple generations of backcrossing, to increase the resistance of wheat to FHB. Because the gene is an endogenous gene existing in the cereal crop wheat, the presence of the gene has no influence on the food safety of plants, such that the gene can be used in crop breeding.

In the figure, A is a positive control, that is, wheat germplasm Wangshuibai carrying Tafhb1; B is a transgenic experimental recipient material PH691, and C is a near isogenic line of PH691 carrying Tafhb1.

Figure 3:

FIG. 3 is identification of FHB resistance of transgenic wheat.

In the figure, A is a non-transgenic recipient material PH691, and B is a near isogenic line PH691 carrying Tafhb1.

Figure 4:
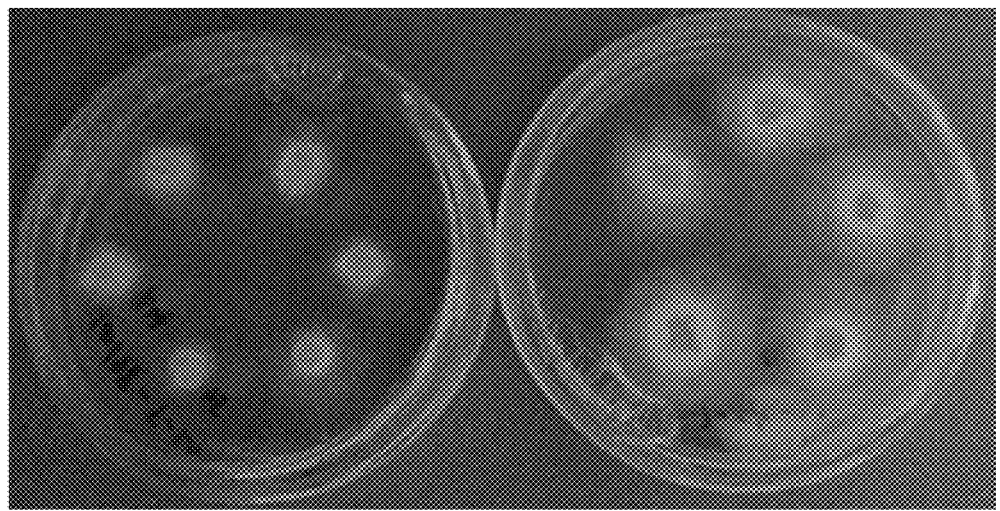

FIG. 4 is identification of FHB resistance of the calli derived from Tafhb1 transgenic wheat.

In the figure, A is the calli derived from Tafhb1 transgenic Shandong Youmai No. 2; and B is the calli derived from non-transgenic Shandong Youmai No. 2.

DETAILED DESCRIPTION

The present invention can be better understood from the examples below. However, it can be understood by those skilled in the art that the examples described is provided merely for illustrating the present invention, instead of limiting the protection scope of the present invention as defined in the claims.

Example 1: Acquisition of FHB1 Candidate Gene

Figure 1:
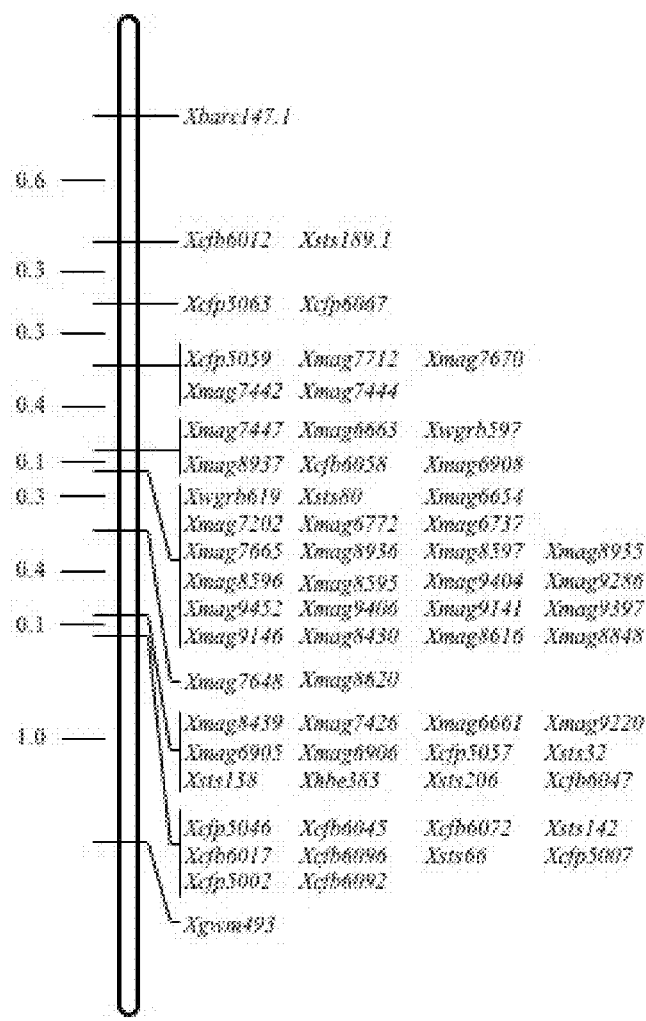
FIG. 1 is a saturated genetic map between Xbarc147.1 and Xgwm493.
Figure 2:
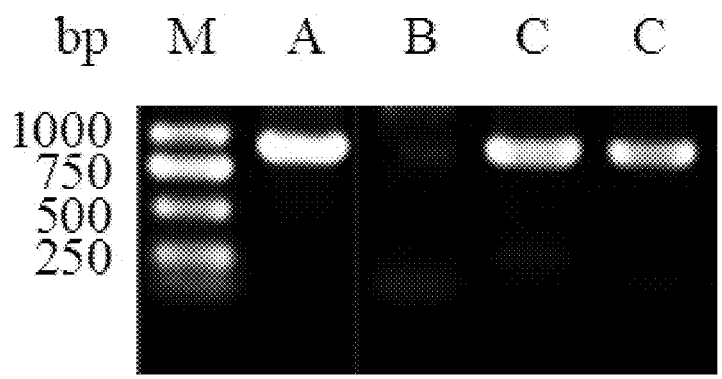
FIG. 2 is PCR detection of transgenic wheat.

Based on the wheat genomic sequence between Xbarc147.1 and Xgwm493 (https://urgi.versailles.inra.fr), 61 pairs of primers with polymorphism between the FHB resistant material Wangshuibai and the FHB susceptible material Nanda 2419 were designed, which are arranged on the chromosome as shown in FIG. 1. The FHB resistance of F7 recombinant inbred line population (father parent: Wangshuibai; mother parent: Nanda 2419) consisting of 530 lines were inoculated with a conidiospore mixture of locally highly pathogenic strains F4, F15, F17 and F34 at equal ratio. 20 μl (about 1000 spores) was injected into the florets just in blooming on middle to top part of the spikes, the spikes were immediately bagged after inoculation and the humidity was maintained, to ensure the occurrence of FHB. 15 days after inoculation, the number of infected spikelets per spike was investigated. Tafhb1 was mapped between the markers Xmag8937 and Xmag9404 according to the number of infected spikelets of different lines. The BAC library of Wangshuibai was screened by Xmag8937 and Xmag9404, to obtain a BAC clone containing the amplified sequence of these two markers. The BAC clone was sequenced by The Beijing Genomics Institute company (BGI), and obtained a 24.6 kb sequence between Xmag8937 and Xmag9404.

Sequence analysis shows that there are 5 open reading frames (ORFs) in this region. It could be known from homology comparison that ORF1 encodes a retrotransposon protein, ORF2 encodes a polyprotein, both ORF3 and ORF5 encode putative proteins, and ORF4 encodes a terpene synthase 7 protein. To determine the candidate gene of Tafhb1 from these 5 genes, the regions between Xmag8937 and Xmag9404 on chromosome 3B of the susceptible material PH691 and the resistant material Sumai No. 3 were sequenced. The results showed that the resistant materials Wangshuibai and Sumai No. 3 have the same sequence in this region, Wangshuibai and PH691 have 4 polymorphic sites, SNP1 does not change the protein encoded by ORF1, SNP2 does not change the protein encoded by ORF2, insertion/deletion site 1 in a gene spacer between ORF3 and ORF4 has no influence on the function of the gene, and insertion/deletion site 2 in ORF5 causes the change of the amino acid encoded. Therefore, it is inferred that ORF5 is the candidate gene of Tafhb1.

Example 2: Acquisition of cDNA Sequence of Tafhb1

The spike cDNA of resistant germplasm Wangshuibai was used as a template. Total RNA was extracted from the wheat spike using a Trizol kit (Introgen), and reversely transcribed using a reverse transcription kit (Promega), to synthesis a single-stranded cDNA. PCR amplification was performed using a primer pair P1 designed based on the ORF5 sequence obtained in Example 1, including a forward primer F: 5'-ATGTGTATATTTGGACAACCATGTAGACAAGC-3' (SEQ ID NO. 3), and a reverse primer R: 5'-TTACAC-GAGTTGCTTCCCGTCACTGGGTTCAGC-3' (SEQ ID NO. 4). The amplification system was 25 µL comprising 5 ng template, 5 pmol of the primers F and R each, 5 nmol of dATP, dTTP, dCTP and dGTP each, 37.3 nmol $MgCl_2$, 0.5 unit DNA polymerase, and 1×PCR buffer. The amplification procedure included denaturation at 94° C. for 3 min; 30 cycles of denaturation at 94° C. for 20 s, annealing at 58° C. for 30 s, and extension at 72° C. for 1 min; and finally extension at 72° C. for 5 min. A 825 bp cDNA nucleotide sequence comprising an open reading frame was obtained by PCR amplification, and the nucleotide was ligated to T-vector at 16° C. for 30 min. The ligation system was 10 µL comprising 1 µL T-vector, 4 µL PCR products, 1 µL ligase, 1 µL ligase buffer, and 3 µL $ddH_2O$. The ligation product was heat shocked at 42° C. for 40 s, transferred to *E. Coli*, and sequenced by BGI. The resultant sequence was as shown in SEQ ID NO:1, and designated as Tafhb1. The protein encoded by the gene is as shown in SEQ ID NO. 2, comprises 274 amino acids, and has a molecular weight of 32.73144 kDalton and an isoelectric point of 10.85.

Example 3: The FHB Resistance of Tafhb1 Transgenic Near Isogenic Line of Wheat is Increased The FHB resistant germplasm Wangshuibai and susceptible wheat material PH691 were crossed, obtained seeds of F1 generation and recurrent parent wheat material PH691. Then the F1 generation seeds were planted and back crossed with PH691, obtained BC1F1 generation seeds and recurrent parent wheat material PH691. Leaves of the two wheat materials were sampled during the seedling stage, DNA was extracted by SDS method (Ma & Sorrells, 1995), and PCR amplification using the primer pair P1. The individual BC1F1 plant with a 825 bp amplified target band was back crossed with PH691 again, obtained BC2F1 generation seeds. After plantation, wheat leaves were sampled during the seedling stage, DNA was extracted, and PCR amplification using the primer pair P1. The individual BC2F1 plant with a 825 bp amplified target band was back crossed with PH691, obtained BC3F1 generation seeds. After plantation, wheat leaves were sampled during the seedling stage, DNA was extracted, and PCR amplification using the primer pair P1. The individual BC3F1 plant with a 825 bp amplified target band was back crossed with PH691, obtained BC4F1 generation seeds. The seeds were planted, the spikes were bagged in the blooming period and inbred once. The DNA was extracted, and 200 pairs of SSR primers having polymorphism between Wangshuibai and PH691 were selected at random over the whole genome (http://wheat.pw.usda.gov/GG3/). A Tafhb1 transgenic near isogenic line of PH691 that is in complete accord with the original transfer recipient PH691 in the amplification band pattern was selected, that is, the transgenic had the same genetic background as the recipient material, and difference only existed in the Tafhb1 section of the two materials. The FHB resistance of the Tafhb1 transgenic near isogenic line and the transfer recipient PH691 was inoculated with a conidiospore mixture of locally highly pathogenic strains F4, F15, F17 and F34 at equal ratio. 20 µl (about 1000 spores) was injected into the florets just in blooming on middle to top part of the spikes, the spikes was immediately bagged after inoculation and the humidity was maintained, to ensure the occurrence of FHB. 15 days after inoculation, the number of infected spikelets per spike was investigated. It was found that the number of infected spikelets of the Tafhb1 transgenic near isogenic line of wheat is obviously less than that of the control wheat material PH691 (FIG. 3, Table 1).

TABLE 1

Number of infected spikelets of transgenic material and transfer recipient material

| Material | Replication | | | | |
|---|---|---|---|---|---|
| | 1 | 2 | 3 | 4 | 5 |
| PH691 | 7.6 ± 0.68 | 5.8 ± 0.42 | 6.1 ± 0.31 | 3.9 ± 0.10 | 7.1 ± 0.50 |
| Tafhb1 transgenic near isogenic line of PH691 | 1.2 ± 0.17* | 1.3 ± 0.22* | 1.1 ± 0.10* | 1.3 ± 0.06* | 1.9 ± 0.10* |

*Significantly different at P = 0.01

Example 4: The FHB Resistance of the Calli of Tafhb1 Transgenic Wheat is Increased The spike cDNA of Wangshuibai in blooming was used as a template. PCR amplification was performed using the primer pair P1. The amplified PCR product was cut by the restriction endonuclease XbaI, and ligated to the PBI121 expression vector cut by the same restriction endonuclease, to obtain a plasmid vector initiated by the Ubiqutin promotor for over expression of Tafhb1. The constructed vector was transferred to *E. Coli* strain DH5α by heat shock, and screened in LB medium containing 50 μg/mL kanamycin, to obtain a positive clone. With reference to the materials and methods described in Weeks, *Plant Physiol*, Vol 102, Page 1077-1084, 1993, the Tafhb1 gene under control of Ubiqutin promotor was transformed into susceptible wheat material Shangdong Youmai No. 2 by particle bombardment, and the calli after transformation by particle bombardment were screened in ½ MS medium containing 30 mg/L G418, to obtain wheat calli resistant to G418. This suggests that the transformation vector is integrated into the cellular chromosome of wheat calli, and the exogenous gene is expressed in the cells, such those the calli acquires the G418 resistance. The FHB resistance of the resistant calli was investigated. The results showed that the FHB resistance of the transgenic resistant calli was increased compared with that of the nontransgenic Shangdong Youmai No. 2 calli (FIG. 4).

What is claimed is:

1. A transgenic wheat plant comprising a recombinant construct comprising the polynucleotide sequence of SEQ ID NO: 1 operably linked to a heterologous promoter, wherein the transgenic wheat plant has improved *Fusarium* head blight resistance compared to a control wheat plant that does not comprise said recombinant construct.

2. A transgenic Triticeae plant comprising a recombinant construct comprising the polynucleotide sequence of SEQ ID NO: 1 operably linked to a heterologous promoter, wherein the transgenic Triticeae has improved *Fusarium* head blight resistance compared to a control Triticeae plant that does not comprise said recombinant construct.

3. A transgenic plant comprising a recombinant construct comprising the polynucleotide sequence of SEQ ID NO: 1 operably linked to a heterologous promoter, wherein the transgenic plant has improved *Fusarium* head blight resistance compared to a control plant that does not comprise said recombinant construct.

* * * * *

SEQUENCE LISTING

```
<160> NUMBER OF SEQ ID NOS: 4

<210> SEQ ID NO 1
<211> LENGTH: 825
<212> TYPE: DNA
<213> ORGANISM: Wheat Cultivar Wangshuibai

<400> SEQUENCE: 1
atgtgtatat ttggacaacc atgtagacaa gctgttggac gtctgttttg ggctcacgtc      60
gtgcaaatgg tcgaggacaa gaagaagaga ctccttgaga agaaggaagc tccactgaaa     120
tggcagcaga aactggaagg ggcaattaag gccactgaag aaaaggagaa gaagctcaag     180
tcgaaaaagc acaggaggcg aagctattct tcctcagaat ccgacagtga atccgagagc     240
gacagtgatc ggaaacgcag gaagaggaag gaccgcaaaa ggcacaaaaa acatggccac     300
tctgactctg atggtgccag gaggcgcaag cacaggtcaa agaggaggag ctcggactct     360
agcgatgaga gcgacagtga tgaatatgat agcgaatctg aagaggatcg ccgaaggaag     420
aagcactcgc acaggaggaa gcatcgccgg cactcttcaa ggtcagagtc tgatgcttca     480
gattacagca gcgatgatga tgagcggaga tcaaccagga aggaccacac taggagccgc     540
aggcgtcgcc accgatcctc agacgatgaa tctgaggaga agatcaggtt gaggcatagg     600
aagcgtcaca gatcaagtga cgaggacaag ccgtcagatt ctgacaacca taagcgtcac     660
aggagccgct ctatgtcctt ggatgacggt gctgctggcg agccagacaa gatgaatgat     720
ggcaaggggt ctcacaaaag ccggcaccac cgccgccacc accatcacca tcatgatcat     780
cgtgcgaact ctgctgaacc cagtgacggg aagcaactcg tgtaa                     825

<210> SEQ ID NO 2
<211> LENGTH: 274
<212> TYPE: PRT
<213> ORGANISM: Wheat Cultivar Wangshuibai

<400> SEQUENCE: 2

Met Cys Ile Phe Gly Gln Pro Cys Arg Gln Ala Val Gly Arg Leu Phe
1               5                   10                  15

Trp Ala His Val Val Gln Met Val Glu Asp Lys Lys Arg Leu Leu
            20                  25                  30

Glu Lys Lys Glu Ala Pro Leu Lys Trp Gln Gln Lys Leu Glu Gly Ala
        35                  40                  45

Ile Lys Ala Thr Glu Glu Lys Glu Lys Lys Leu Lys Ser Lys His
    50                  55                  60

Arg Arg Arg Ser Tyr Ser Ser Ser Glu Ser Asp Ser Glu Ser Glu Ser
65                  70                  75                  80

Asp Ser Asp Arg Lys Arg Arg Lys Arg Lys Asp Arg Lys Arg His Lys
                85                  90                  95
```

-continued

```
Lys His Gly His Ser Asp Ser Asp Gly Ala Arg Arg Arg Lys His Arg
            100                 105                 110

Ser Lys Arg Arg Ser Ser Asp Ser Ser Asp Glu Ser Asp Ser Asp Glu
        115                 120                 125

Tyr Asp Ser Glu Ser Glu Glu Asp Arg Arg Arg Lys Lys His Ser His
    130                 135                 140

Arg Arg Lys His Arg Arg His Ser Ser Arg Ser Glu Ser Asp Ala Ser
145                 150                 155                 160

Asp Tyr Ser Ser Asp Asp Asp Glu Arg Arg Ser Thr Arg Lys Asp His
                165                 170                 175

Thr Arg Ser Arg Arg Arg Arg His Arg Ser Ser Asp Asp Glu Ser Glu
            180                 185                 190

Glu Lys Ile Arg Leu Arg His Arg Lys Arg His Arg Ser Ser Asp Glu
        195                 200                 205

Asp Lys Pro Ser Asp Ser Asp Asn His Lys Arg His Arg Ser Arg Ser
    210                 215                 220

Met Ser Leu Asp Asp Gly Ala Ala Gly Glu Pro Asp Lys Met Asn Asp
225                 230                 235                 240

Gly Lys Gly Ser His Lys Ser Arg His His Arg Arg His His His His
                245                 250                 255

His His Asp His Arg Ala Asn Ser Ala Glu Pro Ser Asp Gly Lys Gln
            260                 265                 270

Leu Val

<210> SEQ ID NO 3
<211> LENGTH: 32
<212> TYPE: DNA
<213> ORGANISM: Artificial Sequence
<220> FEATURE:
<223> OTHER INFORMATION: Forward primer F

<400> SEQUENCE: 3
atgtgtatat ttggacaacc atgtagacaa gc                                 32

<210> SEQ ID NO 4
<211> LENGTH: 33
<212> TYPE: DNA
<213> ORGANISM: Artificial Sequence
<220> FEATURE:
<223> OTHER INFORMATION: Reverse primer R

<400> SEQUENCE: 4
ttacacgagt tgcttcccgt cactgggttc agc                                33
```